United States Patent [19]

Falke et al.

[11] 4,379,083

[45] Apr. 5, 1983

[54] PROCESS FOR THE PREPARATION OF BLOOD PLASMA FRACTIONS

[75] Inventors: Jürgen Falke; Helmut Geiger, both of Marburg; Wolfgang Grünbein, Liederbach; Heinz-Georg Kandel, Wetter, all of Fed. Rep. of Germany

[73] Assignee: Behringwerke Aktiengesellschaft, Marburg, Fed. Rep. of Germany

[21] Appl. No.: 263,719

[22] Filed: May 14, 1981

[30] Foreign Application Priority Data

May 16, 1980 [DE] Fed. Rep. of Germany ....... 3018669

[51] Int. Cl.$^3$ ................................................. C07G 7/00
[52] U.S. Cl. ................................. 260/112 B; 210/927
[58] Field of Search ....................... 260/112 B, 112 R; 210/927, 712

[56] References Cited

U.S. PATENT DOCUMENTS 3,764,009 10/1973 Watt ........................................ 210/96
4,066,549 1/1978 Oeser ..................................... 210/177

*Primary Examiner*—Allan Lieberman
*Assistant Examiner*—Patricia Short
*Attorney, Agent, or Firm*—Curtis, Morris & Safford

[57] ABSTRACT

A precipitation process for the preparation of blood plasma constituents is disclosed, wherein the plasma to be fractionated and the precipitant are circulated in a closed system.

3 Claims, 1 Drawing Figure

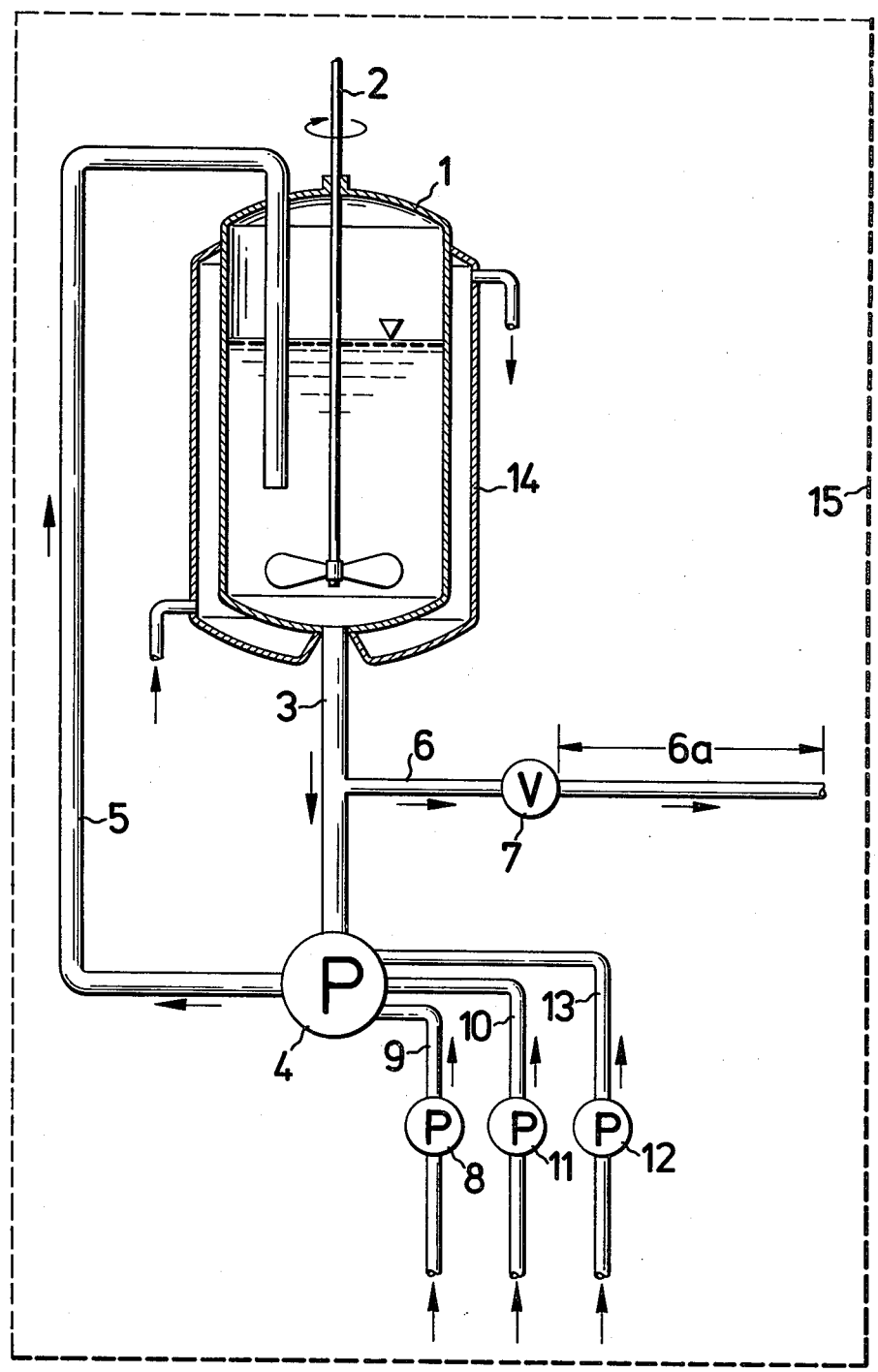

PROCESS FOR THE PREPARATION OF BLOOD PLASMA FRACTIONS

The present invention relates to a process for the preparation of plasma fractions by precipitation.

Albumins and globulins are being used in human and veterinary medicine for some application purposes. These proteins are obtained from human or animal plasma by fractional precipitation. The precipitation process has been carried out hitherto in the following manner: The plasma was placed initially batchwise into the reaction vessel and the precipitant was metered in slowly thus causing the individual fractions to precipitate. The disadvantages of this discontinuous process reside in the fact that it is very time-consuming because of the long dwell times required and that it yields only difficulty separable precipitates.

It was therefore a task to provide a fractionation process which should yield easily separable precipitates within an acceptable period of time.

It has now been found that this task can be solved when circulating the plasma to be fractionated, the precipitant and the buffer in a closed system.

Subject of the present invention, consequently, is a process for the preparation of plasma fractions by mixing plasma with a precipitant, at a constant temperature and in the presence of a buffer, followed by separation of the precipitated plasma protein, which comprises circulating the mixture consisting of plasma, precipitant, buffer and precipitated protein, in a loop reactor consisting of a closed tube circuit connected with a circulating pump.

The particular features of this process reside in the fact that the mixture consisting of plasma, precipitant, buffer and precipitated protein is circulated in a loop reactor consisting of a stirring tank, the outlet of which is connected with the inlet of a circulating pump and the inlet of which is connected with the outlet of this circulating pump, that the plasma, the precipitant and the buffer are conveyed to the system separately in a zone of high turbulence and that a quantity of reaction mixture corresponding to the total quantity of plasma, precipitant and buffer metered in is withdrawn continuously from the system via a branch pipe located between the outlet of the stirred tank and the inlet of the pump.

The process according to the invention is carried out in a "loop-type" reactor. This loop reactor consists of a stirring tank and pipings forming a closed circular system, a circulating pump being connected with this system.

A further feature of this process is that the reaction mixture withdrawn from the loop reactor flows through a dwell zone prior to the separation of the precipitated protein.

The stirring tank corresponds to those commonly used. It is provided with means for measuring and controlling the temperature and the pH of the precipitant, for heating or cooling, respectively, the contents of the tank and for stirring up the contents of the tank. Heating or cooling may be done by a double jacket or by exterior or interior tube coils and the like. The contents of the tank are stirred up by agitator means driven by a motor, by introducing an inert gas or by means of the impulse of the precipitant added. The inlet and the outlet for the medium kept circulating may be arranged at any point, preferably, however, the outlet is located at the bottom of the tank and the inlet pipe entering into the tank at the head ends below the liquid level. The outlet of the tank connected with the inlet of a circulating pump and the outlet of this pump is connected with the inlet of the tank. A branch pipe is located between the outlet of the tank and the inlet pipe of the pump. This branch pipe may be shut off by means of a valve. It leads to separating means, for example a filter or a centrifuge. A zone of particular high turbulence, for example, at the pump inlet, is moreover created by the admission pipes for the medium to be fractionated, the precipitant and the buffer, these pipes passing over the metering pumps. As circulating pump there is used a pump with high output, preferably a glandless centrifugal pump, whereas suitable metering pumps are hose pumps, gear pumps, reciprocating pumps or diaphragm pumps.

Depending on the size of the apparatus, the pipes and pumps, too, are maintained at a certain temperature, by a double jacket, or by heating and cooling coils and the like or the whole loop reactor, including the metering pumps, is placed in a room kept at a certain temperature.

Suitable materials for this system are glass, enamel, noncorrosive plastic or metal, for example stainless steel. The material chosen depends in the first place on the size of the system. Small apparatuses may be made completely of metal, glass or enamel.

The size of the stirred tank depends on the quantities of matter to be converted and is in the range of from 0.5 to 100 liters, preferably of from 0.5 to 10 liters. The dimensions of the other parts of the system are adapted in each case to the size of the stirred tank.

The invention will be illustrated, by way of example, in the accompanying drawing representing a flow scheme of the process of the invention, in the description referred to the drawing and in the Examples describing the test procedure.

The preferred design of an apparatus to be used according to the invention can be seen from the drawing. The stirring tank (1) provided with agitator means (2) is connected with the circulating pump (4) via conduit (3). Conduit (5) extending from pump (4) returns to the stirring tank (1). Conduit (6) branching off conduit (3) leads to separating means (not shown in the FIGURE) by passing over dwell zone (6a). Conduit (6) may be sut off by valve (7). The metering pumps (8), (10) and (12) are moreover connected with the inlet of pump (4) by conduits (9), (11) and (13). The stirring tank is kept at a certain temperature by means of a double jacket (14). The whole apparatus may alternatively be placed in a room maintained at a certain temperature, which is indicated by the dotted line (15).

The process according to the invention is used preferably for the fractionation of human or animal plasma or plasma fractions, respectively, but it may also be used for the fractionation of other protein matter.

The precipitant chosen has to be adapted to the material to be precipitated, $(NH_4)_2SO_4$ solution, alcohol such as ethanol or a polyether alcohol, for example polyethylene glycol, being used preferably for human or animal plasma. The quantity of the precipitant, too, depends on the nature and on the quantity of the protein fractions to be precipitated and may be determined by a preliminary test.

An acid or an alkaline liquor or a commercial buffer, respectively, is used for maintaining the optimal pH for the precipitation process.

The mixture consisting of the medium to be fractionated, the precipitant, the buffer and the precipitated protein is withdrawn from the stirred tank by means of the circulating pump and recycled thereto at another point. Part of this mixture is continuously withdrawn from the stirred tank through the branch pipe and is passed to the separating means, where the precipitated protein is separated from the mixture. The corresponding total quantity of the medium to be fractionated, of precipitant and buffer is simultaneously conveyed to the system by means of the metering pumps so that the material balance in the system is substantially in equilibrium. The individual components may be metered in continuously or at intervals, it being important that possible fluctuations of the concentration in the whole loop reactor be within the acceptable limits for the protein fraction to be precipitated.

The process according to the invention yields protein flocks that can be easily separated. When there is used a centrifuge for the separation process, the recipient may be emptied continuously, since the centrifugal forces required for separating the protein flocks are very little. The output in the apparatus according to the invention may be increased to a multiple of that reached in the known precipitation processes, owing to the fact that the residence time in the loop reactor is short. It has moreover been shown that the process of the invention does not involve an increased danger of a bacterial invasion which would have to be expected in the case of fairly long operation times.

EXAMPLE 1

The stirring tank (1) according to the accompanying drawing is made of glass, has a volume of 1.5 liters, is doublewalled and is kept at a temperature of $-2°$ C. Conduits (3) and (5) consist of insulated glass doublepipes. The contents of the stirring tank (1) and of the conduits (3) and (5) are made circulate by the glandless centrifugal pump (4) at a rate of 200 liters/h. The hose pumps (8), (10) and (12) convey to the system 800 ml/h of a human plasma, 93 ml/h of ethanol, and a commercial buffer (pH 4.8) in a quantity such that a pH of 7.4 is reached in the system. 900 ml/h of reaction liquid are withdrawn continuously from the system through valve (7) and subsequently submitted to centrifugation, whereby there are separated about 10 g/h of an enriched fibrinogen fraction.

EXAMPLE 2

The apparatus used is analogous to that of Example 1, except that the vessel has a volume of 3.0 liters. 800 ml/h of human plasma, 280 ml/h of ethanol and buffer solution are conveyed to this apparatus at a temperature of $-6°$ C. at pH 7.6, while 1,000 ml/h of reaction liquid are withdrawn. There are obtained about 50 g/h of an enriched immunoglobulin fraction.

What is claimed is:

1. A process for the preparation of a plasma constituent which comprises separately and continuously feeding plasma, precipitant and buffer to a circulating pump for admixture in a zone of high turbulence and introduction to a loop reactor comprising said pump, a stirring vessel, a conduit extending from an outlet of the vessel to the pump, and a recirculating conduit extending from the pump to an inlet of said vessel for circulating the mixture to and from said vessel, and continuously withdrawing a portion of the reaction mixture from the loop reactor for separation of a precipitated plasma protein.

2. The process defined in claim 1 in which the reaction mixture is withdrawn from the loop reactor as it passes from the stirring vessel to the pump.

3. The process as claimed in claim 1, wherein the reaction mixture withdrawn from the loop reactor flows through a dwell zone prior to the separation of a precipitated plasma protein.

* * * * *